US00RE34439E

United States Patent [19]

Heath

[11] E Patent Number: Re. 34,439

[45] Reissued Date of Patent: Nov. 9, 1993

[54] DENTAL COMPACTOR INSTRUMENT

[76] Inventor: Derek E. Heath, 1917 Sherwood Dr., Johnson City, Tenn. 37601

[21] Appl. No.: 668,911

[22] Filed: Mar. 13, 1991

Related U.S. Patent Documents

Reissue of:

[64] Patent No.: 4,871,312
Issued: Oct. 3, 1989
Appl. No.: 267,531
Filed: Nov. 4, 1988

[51] Int. Cl.[5] ..... A61C 3/08

[52] U.S. Cl. ..... 433/164; 433/81; 433/102

[58] Field of Search ..... 433/81, 102, 164, 224

[56] References Cited

U.S. PATENT DOCUMENTS

| | | | |
|---|---|---|---|
| 1,307,446 | 6/1919 | Kerr | 433/102 |
| 1,694,857 | 12/1924 | Kulik | 433/81 |
| 4,299,571 | 11/1981 | McSpadden | 433/102 |
| 4,332,561 | 6/1982 | McSpadden | 433/102 |
| 4,353,698 | 10/1982 | McSpadden | 433/164 |
| 4,457,710 | 7/1984 | McSpadden | 433/81 |
| 4,538,989 | 9/1985 | Apairo, Jr. et al. | 433/102 |

FOREIGN PATENT DOCUMENTS

| | | | |
|---|---|---|---|
| 279144 | 10/1914 | Fed. Rep. of Germany | 433/102 |
| 365050 | 12/1922 | Fed. Rep. of Germany | 433/102 |
| 2724516 | 4/1978 | Fed. Rep. of Germany | 433/81 |
| 775073 | 10/1934 | France | 433/102 |

*Primary Examiner*—John J. Wilson
*Attorney, Agent, or Firm*—Bell, Seltzer, Park & Gibson

[57] ABSTRACT

A dental instrument adapted to be used as a dental compactor for condensing a thermoplastic material in the extirpated root canal of a tooth. The dental compactor instrument is formed with a tapered shank or working portion having at least two helical flutes defining at least two continuous helical shoulders. A helical peripheral land extends between adjacent helical flutes at the periphery of the shank. The shoulders have a neutral rake angle at the periphery of the shank.

11 Claims, 2 Drawing Sheets

DENTAL COMPACTOR INSTRUMENT

Matter enclosed in heavy brackets [ ] appears in the original patent but forms no part of this reissue specification; matter printed in italics indicates the additions made by reissue.

The present invention relates to the field of dental instruments and more particularly to compactor instruments used in endodontia for obturating and compacting an extirpated tooth root canal with a thermoplastic material.

The obturating (filling) of a stripped (expirated) tooth root canal can be a technically difficult and delicate procedure. The extirpated tooth root canal must be filled in a homogenious three-dimensional manner without voids in order to prevent leakage or communication between the root canal and the surrounding tissues of the tooth.

In the typical or traditional procedure of obturating a tooth root canal, strand-like pieces of a thermoplastic material, conventionally gutta percha, known as points, are inserted into a stripped tooth root canal. These gutta percha points are physically compacted by small manually actuated instruments known as "pluggers" and "spreaders", or by machine driven "compactors".

While the known compactors provide excellent results when operated by a skilled endodontist, misuse can damage the root canal walls and excessive and misdirected pressure can be developed which will cause the thermoplastic material to breech the apical foramen or to result in failure to fill side canals.

An object of the present invention is to provide a compactor instrument which is of improved flexibility so as to reduce the forces exerted on the wall of the stripped tooth root canal.

It is another object of the present invention to provide a compactor instrument which more accurately tracks the path of the stripped tooth root canal.

Yet another object of the present invention is to provide a compactor instrument which will not readily cut into the wall of the root canal.

More particularly, the present invention provides a dental compactor instrument for compacting a thermoplastic material in a tooth root canal, having a shank terminating at a pilot end, and a tapered working portion along at least a portion of the length of the shank. The tapered working portion is formed with at least two continuous helical flutes defining two continuous shoulders. A helical land is defined at the periphery of the working portion extending between adjacent flutes. The juncture of the flute shoulders and land defines a substantially neutral rake angle.

A more complete understanding of the present invention will be had by reference to the specification and accompanying drawings wherein like numerals refer to like parts throughout and in which.

The Figures illustrate a dental instrument used as a dental compactor for condensing a thermoplastic material, such as gutta percha, in a stripped tooth root canal upon rotation of the instrument.

Figure 1:
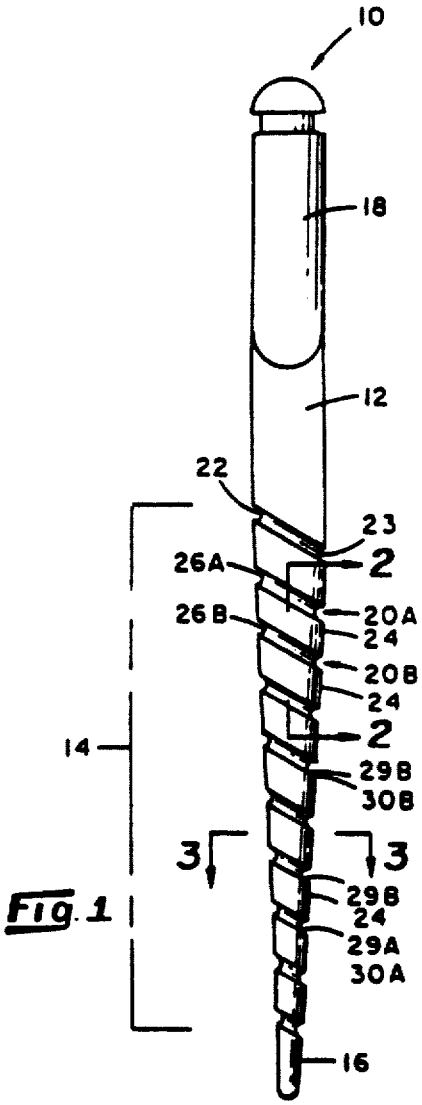
FIG. 1 illustrates a side view of one embodiment of a dental compactor instrument embodying features of the present invention.
Figure 2:
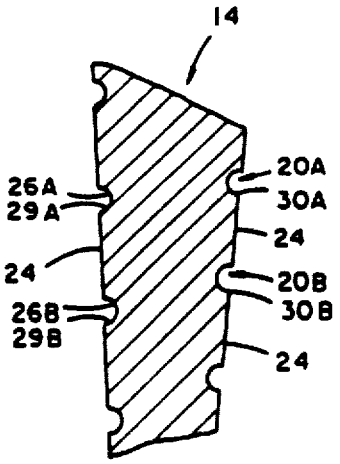
FIG. 2 is an enlarged sectional view of the dental compactor instrument as seen in the direction of arrows 2—2 in FIG. 1.
Figure 3:
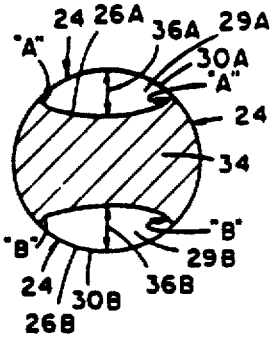
FIG. 3 is a transverse cross-sectional view as seen in the direction of arrows 3—3 in FIG. 1.

With reference to FIGS. 1 through 3, the compactor instrument, generally denoted as the numeral 10, has a shank 12 and a working portion 14 which is tapered along at least a portion of the length of the shank 12 to a tapered pilot end 16. The shank 12 above the working portion 14 is shown as being substantially cylindrical. A fitting 18 is attached to the upper cylindrical part of the shank 12 which is adapted to mate with a chuck of a dental handpiece (not shown).

As shown in FIGS. 1 and 2, two continuous helical flutes 20A and 20B are formed in and along the working portion 14 of the shank 12. Hereinafter, the flutes are referred to as a first flute 20A and second flute 20B. The second flute 20B originates at a location, denoted as the numeral 22, 180° around the circumference of the shank 12 at the top end of the working portion 14 from the origination region, denoted as the numeral 23, of the first flute 20A. Each flute 20A and 20B is continuous along the length of the working portion 14 to the pilot end 16 of the shank 12 and are oppositely disposed to each other.

The first flute 20A and second flute 20B cooperate to define a continuous helical land 24 at the periphery of the working portion 14 of the shank 12 extending between flutes 20A an 20B.

The flutes should preferably be of uniform pitch and of a constant width. The lands should preferably be at least about 0.004 inches. However, the flutes may be formed with a constant helix angle which will cause the pitch to vary.

With reference particularly to FIG. 2, it can be more clearly seen that the flutes 20A and 20B are each generally U-shaped in transverse cross-section of the flute. That is, the first flute 20A has an arcuately concave wall 26A and the second flute 20B has an arcuately concave wall 26B. The first flute 20A forms a helical shoulder 29A at the periphery of the shank 12, and the second flute 20B forms a helical shoulder 29B at the periphery of the shank 12.

The intersection or juncture of each of the shoulders 29A and 29B with the land 24 at the periphery of the working portion 14 of the shank 12 is blunt or dull so as to provide smooth helical edges 30A and 30B, respectively. Preferably, the edges are smoothly radiused.

Now with reference to FIG. 3, there is shown a transverse cross-sectional view of the working portion 14 of the shank 12. The first flute 20A and second flute 20B cooperate to define a web 34 therebetween. The web 34 has a first radial web clearance generally denoted as the numeral 36A from land 24, and a second radial web clearance, generally denoted as the numeral 36B from the land 24. In transverse cross-section of the shank 12, both the wall 26A of the first flute 20A and wall 26B of the second flute 20B defining the walls of the web 34, are generally concave relative to the periphery of the shank 12. The flute wall 26A of the first flute 20A intersects the periphery of the shank 12 in two regions each denoted by the letter "A" immediately adjacent the shank periphery at an angle of substantially 90 degrees to the tangent of the shank periphery to form what is commonly referred to as a substantially zero or neutral rake angle flute. As shown, each region "A" lays substantially on a radius of the shank 12. The flute wall 26B of the second flute 20B also intersects the periphery of the shank 12 in two regions each denoted by the letter "B" immediately adjacent the shank periphery at an angle of substantially 90 degrees to the tangent of the shank periphery to form what is commonly referred to as a zero or neutral rake angle flute. As shown, each region "B" lays substantially on a radius of the shank 12.

Figure 5:
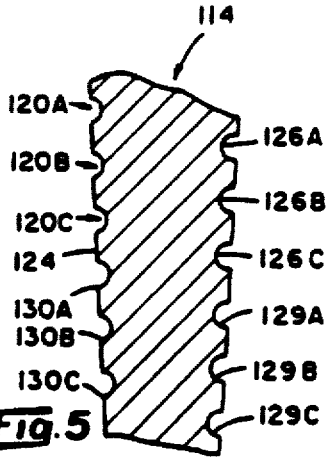
FIG. 5 is an enlarged sectional view of the dental compactor instrument as seen in the direction of arrows 5—5 in FIG. 4.
Figure 6:
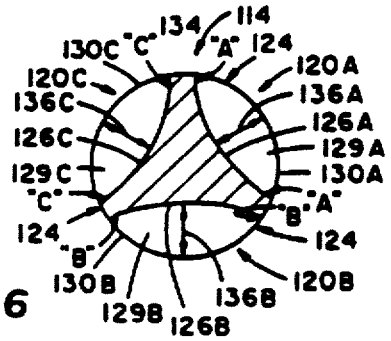
FIG. 6 is a transverse cross-sectional view as seen in the direction of arrows 6—6 in FIG. 4.
Figure 4:
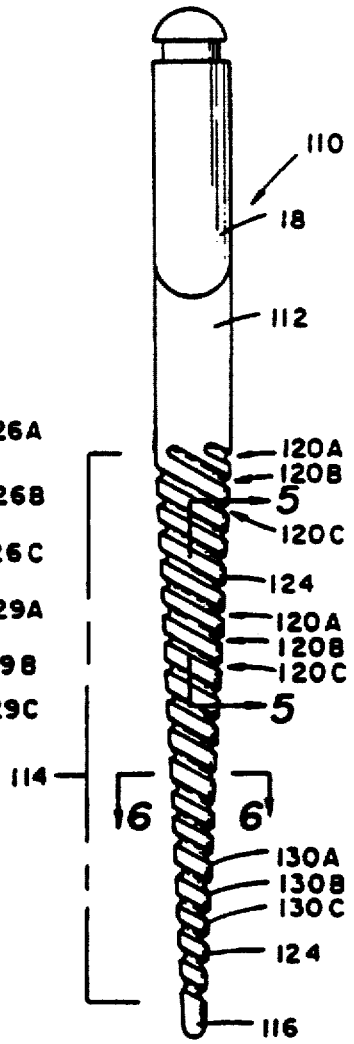
FIG. 4 illustrates a side view of another embodiment of a dental compactor instrument embodying features of the present invention.

With reference to FIGS. 4–6, there is illustrated a dental compactor instrument 110 similar to the dental compactor instrument 10 of FIGS. 1 through 3 in every respect except that the tapered shank 112 of the instrument 110 is formed with three continuous helical flutes 120A, 120B, and 120C along the tapered working portion 114 of the shank 112. Hereinafter, the flutes are referred to as first flute 120A, second flute 120B, and third flute 120C. The first flute 120A, second flute 120B and third flute 120C each originate at separate locations equally spaced apart around the circumference of the shank 112 at the top end of the working portion. Each flute 120A, 120B and 120C is continuous along the length of the working portion 114 to the pilot end 116 of the shank 112.

The first flute 120A, second flute 120B, and third flute 120C cooperate to define three continuous helical lands 124 at the periphery of the working portion 114 of the shank 112 extending between adjacent flutes.

The flutes should preferably be of uniform pitch and of a constant width. The lands should preferably be at least about 0.004 inches. Again, however, the flutes may be formed with a constant helix angle.

With reference particularly to FIG. 5, it can be more clearly seen that the flutes 120A, 120B, and 120C are each generally U-shaped in transverse cross-section of the flute. That is, the first flute 120A has an arcuate concave wall 126A, the second flute 120B has an arcuate concave wall 126B, and the third flute 120C has an arcuate concave wall 126C. The first flute 120A forms a helical shoulder 129A at the periphery of the shank 112, the second flute 120B forms a helical shoulder 129B at the periphery of the shank 112, and the third flute 120C forms a helical shoulder 129C at the periphery of the shank 112.

The intersection or juncture of each of the shoulders 129A, 129B, 129C with the lands 124 at the periphery of the working portion 114 of the shank 112 is blunt or dull so as to provide smooth helical edges 130A, 130B and 130C, respectively. Preferably, the edges are smoothly radiused.

Now with reference to FIG. 6, there is shown a transverse cross-sectional view of the working portion 114 of the shank 112. The first flute 120A, second flute 120B and a third flute 120C cooperate to define a web 134 therebetween. The web 134 has a first radial web clearance generally denoted as the numeral 136A from the land 124, a second radial clearance generally denoted as the numeral 136B from the land 124, and a third radial clearance generally denoted as the numeral 136C from the land 124. In transverse cross-section of the shank 112, the wall 126A of the first flute 120A, the wall 126B of the second flute 120B, and the wall 126C of the third flute 120C are each generally concave relative to the periphery of the shank 112. The wall 126A of the first flute 120A intersects the periphery of the shank 112 in two regions each denoted by the letter "A" immediately adjacent the shank periphery at an angle of substantially 90 degrees to the tangent of the shank periphery to form what is commonly referred to as a substantially zero or neutral rake angle flute. As shown, each region "A" lays substantially on a radius of the shank 112. The wall 126B of the second flute 120B intersects the periphery of the shank 112 in two regions each denoted by the letter "B" immediately adjacent the shank periphery at an angle of substantially 90 degrees to the tangent of the shank periphery to form what is commonly referred to as substantially zero or neutral rake angle flute. As shown, each region "B" lays substantially on a radius of the shank 112. The wall 126C of the third flute 120C intersects the periphery of the shank 112 in two regions each denoted by the letter "C" immediately adjacent the shank periphery at an angle of substantially 90 degrees to the tangent of the shank periphery to form what is commonly referred to as a zero or neutral rake angle flute. As shown, each region "C" lays substantially on a radius of the shank 12.

In order to increase the flexibility of the instrument the roots of the flutes can be deeper in the areas in which it is desired to increase flexibility. For example, a No. 40 compactor can be made to have the flexibility of a No. 20 compactor by adjusting the depth of the flutes so that the core approximates that of the smaller sized instrument. Thus, the flutes became deeper as they progress up the shank. In addition to providing increased flexibility, this provides somewhat increased pressure for the thermoplastic filling material.

Figure 8:
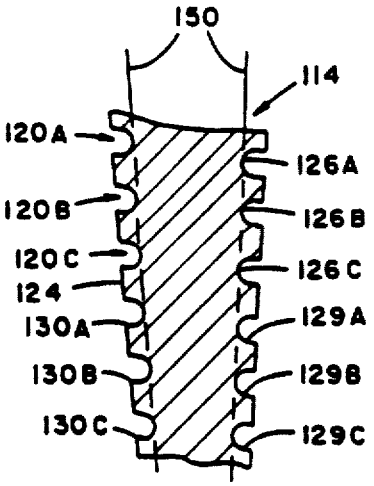
FIG. 8 is a sectional view as seen along lines 8—8 in FIG. 7.
Figure 7:
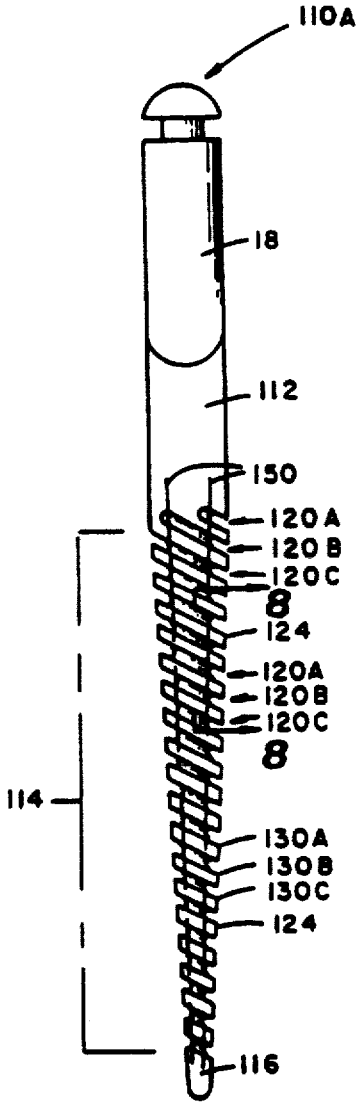
FIG. 7 is a modified instrument along the lines of the instrument shown in FIG. 4.

An example of such an instrument is shown as 110A in FIGS. 7 and 8. The Figures are similar to FIGS. 4 and 5 and have been given the same reference numerals. However, as will be noted by the broken lines 150, the roots of the flutes become deeper as they progress up the shank. Preferably, the included angle between the taper of the working surface of the instrument and the line of the roots of the flutes is from about 1° to 5°. However, it can be varied outside of these limits to obtain special flexibilities.

As shown in FIGS. 1, 4 and 7, the helical flutes are of a left-handed twist so that when the compactor instrument is rotated in a right-handed direction, the shoulders force the thermoplastic material outwardly of the shank and downwardly toward the tip end of the shank. However, it is contemplated that the flutes could follow a right-handed twist if the direction of rotation is left-handed.

The instrument, as concerns lengths, diameter tapers and the like are of course governed by the ISO standards and the U.S. government standards as the case may be.

It has been found that the instruments described above when operated in the manner of those described in U.S. Pat. Nos. 4,353,698 and 4,457,710, provide excellent compaction both laterally and longitudinally. Moreover, because of the construction which provides a strong central web, the instruments have excellent flexibility, improved path finding and bends in a long smooth curve as compared to known instruments of this type.

The instruments in accordance with this invention minimize abrasion on the canal walls and provide added frictional action to plasticize the gutta percha. Moreover, the neutral rake and the U-shape provides excellent control of the plasticized gutta percha and helps insure the adequate obturation of side canals.

The foregoing detailed description is given primarily for understanding of the invention and no unnecessary limitations are to be understood therefrom for modifications will become obvious to those skilled in the art upon reading this disclosure and may be made without departing from the spirit of the invention and scope of the appended claims.

What is claimed is:

1. A dental compactor instrument comprising:

a shank terminating at a pilot tip end;

a tapered working portion along at least a portion of the length of said shank;

flute means formed in the working portion of the shank defining at least two continuous helical flutes having helical shoulders at the periphery of said working portion of said shank;

a helical land at the periphery of the working portion of said shank extending between adjacent flutes; and helical shoulders having a substantially neutral rake angle at the periphery of said working portion of said shank.

2. The dental compactor instrument of claim wherein the width of the lands is over about 0.004 inches.

3. The dental compactor instrument of claim 2, wherein the region of the flute walls defining the neutral rake angle lay substantially on a radius of said working portion of said shank.

4. The dental compactor of claim 2, wherein each of said flutes, in transverse cross-section of said flute, are arcuately concave.

5. The dental compactor instrument of claim 4 wherein the flutes are of variable depth.

6. The dental compactor instrument of claim 1, wherein said flutes are of uniform width and uniform pitch.

*7. A dental compactor instrument comprising*

*a shank terminating at a pilot end and including a working portion extending along at least a portion of the length of the shank adjacent said pilot end;*

*at least one continuous helical flute formed in said working portion of said shank, with said at least one flute defining a curved concave wall when viewed in transverse cross section and a helical shoulder at the periphery of said working portion which faces generally toward said pilot end of said shank, and with said helical shoulder having a substantially neutral rake angle at the periphery of said working portion of said shank; and*

*a helical land at the periphery of the working portion of said shank and extending between adjacent flute segments.*

*8. The dental compactor instrument as defined in claim 7 wherein the width of said land is at least about 0.004 inches.*

*9. The dental compactor instrument as defined in claim 8 wherein said working portion is tapered toward said pilot end.*

*10. The dental compactor instrument as defined in claim 7 wherein said at least one helical flute further defines a pair of helical shoulders which face in generally opposite axial directions, and wherein each of said helical shoulders of said at least one flute has a substantially neutral rake angle at the periphery of said working portion of said shank.*

*11. The dental compactor instrument as defined in claim 7 wherein said helical land has a width which is equal to at least about 50% of the width of said at least one flute when viewed in longitudinal cross section.*

* * * * *